United States Patent [19]

Kafri et al.

[11] Patent Number: 4,810,895

[45] Date of Patent: Mar. 7, 1989

[54] METHOD AND APPARATUS FOR OPTICAL EXAMINATION OF AN OBJECT PARTICULARLY BY MOIRE RAY DEFLECTION MAPPING

[75] Inventors: Oded Kafri; Ilana Glatt, both of Beersheva, Israel

[73] Assignee: Rotlex Optics Ltd., Beer Sheva, Israel

[21] Appl. No.: 154,469

[22] Filed: Feb. 8, 1988

Related U.S. Application Data

[63] Continuation of Ser. No. 3,055, Jan. 13, 1987, abandoned.

[51] Int. Cl.⁴ ............................................. G01N 15/06
[52] U.S. Cl. ...................................... 250/571; 250/572
[58] Field of Search ............ 250/237 G, 550, 562, 563, 571, 572; 356/124.5, 128, 129, 239, 240, 376

[56] References Cited

U.S. PATENT DOCUMENTS

| | | | |
|---|---|---|---|
| 4,139,291 | 2/1979 | Parthasarathy | 250/237 G |
| 4,158,507 | 6/1979 | Himmel | 250/237 G |
| 4,249,823 | 2/1981 | Task | 356/128 |
| 4,459,027 | 7/1984 | Kafri et al. | 250/237 G |
| 4,569,590 | 2/1986 | Karny et al. | 356/128 |
| 4,577,940 | 3/1986 | Krasinski et al. | 356/376 |
| 4,611,917 | 9/1986 | Robieux et al. | 356/376 |
| 4,639,132 | 1/1987 | Glatt et al. | 356/124.5 |

Primary Examiner—David C. Nelms
Assistant Examiner—Stephone B. Allen
Attorney, Agent, or Firm—Benjamin J. Barish

[57] ABSTRACT

A method and apparatus for moire ray deflection mapping for determining properties of an object in which a point source of light producing a diverging beam of direct light is passed through a first optical system including the object to be examined, which system retraces the light in the form of a converging beam of reflected light from the examined object back towards the point source. The converging beam of reflected light is intercepted before reaching the point source and is passed through a second optical system which collimates the beam of reflected light. The collimated beam is then directed through first and second gratings at a preselected angular orientation with respect to each other to produce moire fringe patterns providing an indication of the properties of the examined object. An important advantage in the above novel method is that the same setup can be used for measurements of both phase objects and specular surfaces.

19 Claims, 3 Drawing Sheets

METHOD AND APPARATUS FOR OPTICAL EXAMINATION OF AN OBJECT PARTICULARLY BY MOIRE RAY DEFLECTION MAPPING

This application is a continuation of application Ser. No. 3,055, filed Jan. 13, 1987, now abandoned.

BACKGROUND OF THE INVENTION

The present invention relates to optical examination apparatus, and particularly to a novel method and apparatus for optically examining an object. The invention is particularly useful in moire ray deflection mapping for determining properties of an object, and is therefore described below with respect to this application.

U.S. Pat. No. 4,459,027 by Oded Kafri, one of the inventors of the present application, and Aminadav Livnat, describes a method and apparatus for mapping an object using moire deflectrometry, wherein a collimated beam deflected from the object is used to generate a moire pattern by directing the collimated beam to first and second gratings at a preselected angular orientation and separation with respect to one another, the moire pattern so produced providing an indication of the properties of the examined object.

This technique has proved itself as an efficient, straightforward, and relatively low-cost tool for optical testing. It enables comprehensive diagnostics of optical complements, and is fundamentally compatible with interferometry since the data, namely ray deflection angles, can be translated into phase retardation by integration. The technique applies equally well for phase objects and or specular surfaces, as described for example in O. Kafri and A. Livnat, "Reflective Surface Analysis Using moire Deflectometry", Appl. Optics 20, 3098–3100 (1981). The sensitivity of the method, or alternatively, the spatial resolution, can be enhanced by applying telescopic or microscopic modes of operation, as described in the publications O. Kafri and I. Glatt, "moire Deflectometry—A Ray deflection Approach to Optical Testing", Optical Eng. 24, 944–60 (1985); and J. Krasinski, D. F. Heller, and 0. Kafri, "Phase Object Microscopy Using moire Deflectometry", Appl. Optics 24, 3032–36 (1985), respectively. In the microscopic mode, the beam is expanded after passing through the test object, thus reducing the angular sensitivity and increasing the spatial resolution of the instrument. In the telescopic configuration, on the other hand, a reverse process is carried out, in which the angular resolution is increased at the expense of the spatial resolution.

BRIEF SUMMARY OF THE INVENTION

The present invention provides a novel method and apparatus for optical examination of an object, and especially for moire ray deflection mapping, having a number of advantages, as will be described more particularly below, in the known techniques as described in the above publications.

According to the present invention, there is provided a method of, and apparatus for, moire ray deflection mapping for determining properties of an object, comprising the steps: providing a point source of light producing a diverging beam of direct light; directing the diverging beam of direct light to a first optical system including the object to be examined, which system retraces the light in the form of a beam of reflected light from the examined object back towards the point source of light; intercepting the converging beam of reflected light before reaching the point source of light; passing the intercepted converging beam of reflected light through a second optical system which collimates the beam of reflected light; and examining said collimated beam of reflected light.

The invention is particularly useful, and is therefore described below, in moire ray deflection mapping for determining properties of an object, in which case the collimated beam of reflected light is examined by directing the collimated beam through first and second gratings at a preselected angular orientation and distance with respect to each other to produce moire fringe patterns providing an indication of the properties of the examined object.

One of the important advantages in the above novel method is that the same setup can be used for measurements of both phase objects and specular surfaces.

When the examined object included in the first-optical system mentioned above is a phase object, the retracing of the light in the form of a converging beam is effected by collimating the diverging light beam before passing through the phase object, reflecting the collimated light beam back through the phase object, and converging the collimated light beam after passing back through the phase object. In the described embodiment of the invention examining phase objects, the diverging light beam is passed in one direction through an objective lens to collimate it before passing through the phase object, and the collimated light beam is passed in the opposite direction through the objective lens to converge it after passing through the phase object.

Where the object to be examined is a specular object having a curved specular surface, the retracing step is effected, in the described embodiment, by reflection from the curved specular surface of the examined object.

In both described embodiments, a beam splitter is provided for intercepting the converging beam of reflected light before reaching the point source of light, and for directing the beam through a collimating lens and then through the first and second gratings to produce the moire patterns.

Also in both described embodiments, the focal length of the first optical system is larger than that of the second optical system to reduce the image directed onto the first and second gratings, thereby increasing the angular resolution.

As described above, one of the important advantages in the novel method and apparatus is that the same setup can be used for measurements of both phase objects and specular surfaces. Another important advantage is that by moving the mentioned lens in the first optical system, paraxial approximation condition can be maintained, thereby enabling measurement of specular objects having highly curved surfaces or phase objects having short focal-length lenses. A still further advantage, also mentioned above, is that by making the focal length of the first optical system larger than that of the second optical system, the image directed through the first and second gratings can be reduced, thereby increasing angular resolution.

Further features and advantages of the invention will be apparent from the description below.

BRIEF DESCRIPTION OF THE DRAWINGS

The invention is herein described, by way of example only, with reference to the accompanying drawings wherein.

BRIEF DESCRIPTION OF THE PRIOR ART TECHNIQUES

Figure 1:
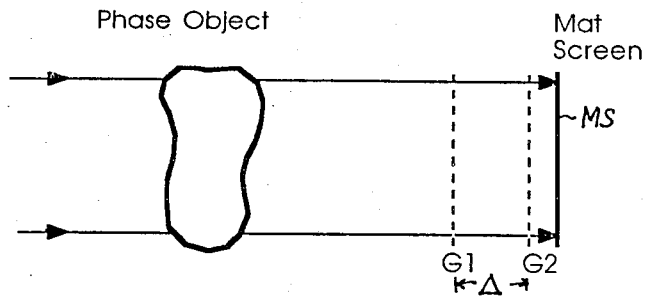
FIGS. 1 and 2 illustrate prior-art setups for ray deflection analysis of phase objects and specular objects, respectively, for example as described in the above-cited publications.
Figure 2:
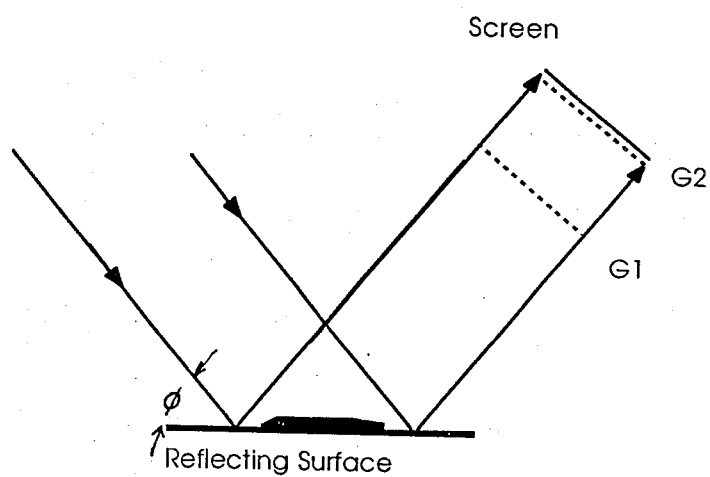

FIGS. 1 and 2 illustrate the classical approach to a moire deflectometer design which requires different setups for testing of phase objects and reflective objects. In the basic setup for phase objects as illustrated in FIG. 1, a collimated beam passes through the examined object and then traverses the set of gratings $G_1$ and $G_2$ of identical pitch p, separated by a distance $\Delta$. The moire pattern is formed by the overlap of the shadows of the first grating with the second grating and is viewed on a mat screen MS attached to grating $G_2$.

To analyze reflective surfaces, the setup is modified as illustrated in FIG. 2. in which the collimated beam is first projected onto a specular surface at an angle $\phi$, and the reflected beam passes through the gratings $G_1$, $G_2$. The latter setup suffers from an inherent distortion $1 \times \cos \phi$ in one axis. In addition other interfering effects as shadowing might occur at higher angles.

Further details of the known techniques for moire ray deflection mapping are available in the literature, for example in the above-cited U.S. Pat. No. 4,459,027 and in the two above-cited publications.

DESCRIPTION OF PREFERRED EMBODIMENTS OF THE INVENTION

Figure 3:
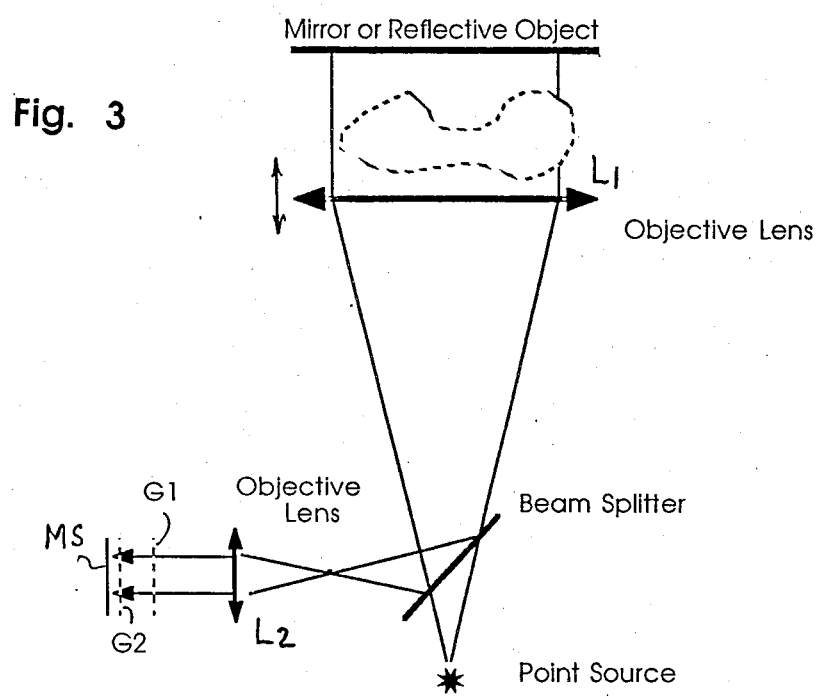
FIG. 3 illustrates moire ray deflection apparatus for determining the properties of a phase object in accordance with the present invention.
Figure 4:
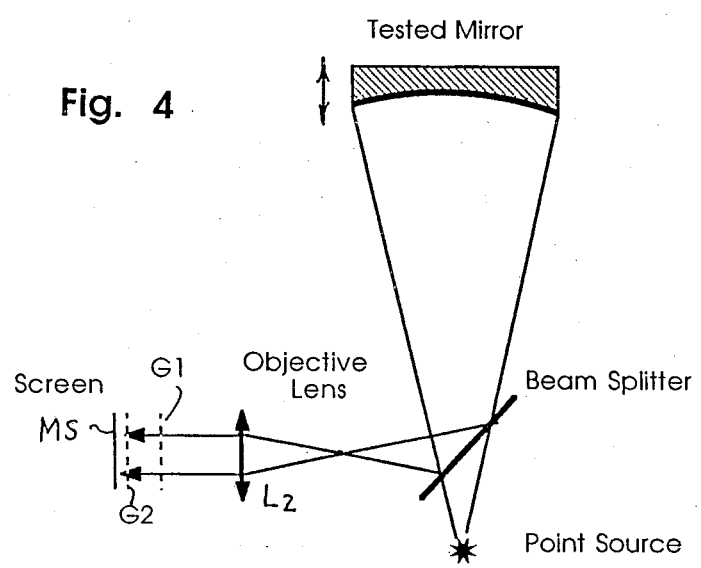
FIG. 4 illustrates moire ray deflection apparatus for determining the properties of a specular object, such as a curved mirror, in accordance with the present invention.

As mentioned earlier, the present invention enables substantially the same setup to be used for measurements of both phase objects and specular objects. FIG. 3 illustrates a setup for measuring phase objects, whereas FIG. 4 illustrates a setup for measuring specular objects having curved specular surfaces.

The apparatus illustrated in FIG. 3 comprises a point source light 2 which produces a diverging beam of light. The diverging beam of light passes through a beam splitter 4 and is directed to an optical system, generally designated 10, which includes the phase object to be examined, the latter object being designated 12.

Optical system 10 further includes an objective lens 14 which collimates the light from the point source 2 before the light passes through the phase object 12, and a flat reflective surface 16 which reflects the light passing through the phase object 12 back through the phase object to the objective lens 14. The latter lens converges the reflected beam after passing through the phase object 12 and directs it back towards the point source 2. Optical system 10, including objective lens 14, the examined phase object 12, and the reflective surface 16, thus causes the light beam, after passing twice through the phase object 12, to be retraced, in the form of a converging beam, back towards the point source of light 2.

Beam splitter 4 intercepts the converging beam of reflected light before reaching the point source 2 and directs the beam to a second optical system, generally designated 20, including a second objective lens 22. Optical system 20 collimates the beam reflected from beam splitter 4 and directs the collimated beam through first and second gratings $G_1$, $G_2$, at a preselected angular orientation and distance with respect to each other, to produce moire patterns on the mat screen MS attached to grating $G_2$. The latter moire patterns may be used, according to known techniques, to provide an indication of the properties of the examined phase object 12.

As illustrated in FIG. 3, the focal length of optical system 10 is larger than that of optical system 20, thereby reducing the image directed through the first and second grating $G_1$, $G_2$. As mentioned earlier, this increases the sensitivity; improvements in angular resolution of one order of magnitude have been observed. In addition, lens 14 in optical system 10 may be mounted so as to be movable toward and away from the examined phase object 12, to maintain paraxial approximation, thereby enabling the apparatus to be used for short focal-length lenses.

The setup illustrated in FIG. 3 is thus unlike the classical deflectometer setup where beam expansion is achieved by a reverse telescope, comprising a microscope objective and an of-axis telescope mirror attached to a laser. Rather the setup illustrated in FIG. 3 uses a Newtonian-type telescope (like the Fizeau interferometer). After the laser beam is expanded to the required width, passing through the large objective lens 14, it passes through the phase object 12 (assuming that it remains parallel within the paraxial approximation), and is then reflected back into the telescope by the flat mirror 16, thus passing twice through the phase object. The retraced beam is diverted 90° by beam splitter 4 to the smaller objective lens 20 where it is recollimated. Now a small diameter deflectometer may be used to detect ray deflections.

The setup illustrated in FIG. 3 can be easily modified to measure flat specular objects simply by replacing the flat reflector by the object to be examined. The optical system including the examined object may also include a large objective lens, corresponding to lens 14 in FIG. 3, but this is not essential in a set-up for examining a concave specular object, and therefore such a lens has been omitted in FIG. 4.

Thus as illustrated in FIG. 4, a point source of light 102, such as a laser, produces a diverging beam of direct light which, after passing through beam splitter 104, is directed to an optical system, generally designated 110, which, as in the FIG. 3 embodiment, retraces the light in the form of a converging beam from the examined object back towards the point source 102. In this case, however, optical system 110 does not include a large objective lens as noted above, and is constituted only of the curved specular surface 112 which is being examined. The converging beam of reflective light from specular surface 112 is intercepted by beam splitter 104 and is passed through a second optical system, generally designated 120. The latter system is constituted of an objective lens 122 which collimates the beam of reflected light and directs the collimated beam to the first and second gratings $G_1$, $G_2$ at preselected angular orientation and distance with respect to each other to produce the moire patterns on the mat screen MS attached to grating $G_2$.

As in the embodiment illustrated in FIG. 3, the optical system 110, particularly the curved specular surface 112, is preferably designed to have a focal length which is larger than that of the second optical system 120 including the objective lens 122; the focal length of the curved specular surface 112 is half its radius of curvature. As also in the FIG. 3 embodiment, the curved specular surface 112 may be mounted for movement towards and away from the point source 102 so that the distance between the point source and the surface is equal to its radius of curvature.

Thus, the setup illustrated in FIG. 4 can also measure surfaces with strong curvature, where the paraxial approximation does not hold. For example, to measure a spherical mirror with a focal length f with the setup of FIG. 4, a large objective lens (corresponding to lens 10 in FIG. 3) may be provided and adjusted so that the convergence of the reflected beam is identical to the divergence of the incident one. Measuring lenses of short focal length can be done in a similar manner with the setup of FIG. 3 as described above, whereas in the known deflectometer setups, such measurements require additional complementary optical elements.

As mentioned earlier, an important advantage of the setups illustrated in FIGS. 3 and 4 is the enhanced sensitivity gained by the inherent telescopic arrangement. As known, if the diameter of the beam emerging from the phase object in the FIG. 3 setup decreases by a factor of M, which is the magnification of the telescope, the ray deflection angle increases by the same factor. Therefore, to obtain the same sensitivity the distances ($\Delta$) between the two gratings can be reduced by a factor M with respect to the conventional moire deflectometer. This results in two immediate advantages. First, the noise due to imperfections of the gratings is reduced; second, the blur due to diffraction is reduced by a factor M.

To demonstrate the effectiveness of the new setup of FIG. 2, the aberrations of a spherical mirror with a focal length of 45 cm were measured. Because of the high deflection angles, the conventional moire deflectometer cannot measure such objects with high sensitivity, unless one adds complementary optical components of high optical quality. In the new setup, however, no extra optical components are required, and one can even dispense with a large objective lens, as shown in FIG. 4. The distance between the point source and the tested mirror is twice the focal length of the mirror; and if the mirror has a perfect spherical surface, the reflected rays would retrace themselves as shown in FIG. 4. The sensitivity of the deflectometer in this configuration is enhanced by the ratio between the focal length of the tested mirror and that of the small objective lens. Namely, a fringe shift, $z'$, from a reference position corresponds to a slope angle $\beta$.

$$\beta = z'\theta/(2\Delta M) \quad (1)$$

where $\theta$ is the intersection angle between the gratings, $\Delta$ is the separation between them, and M is the magnification of the telescope. This equation can be slightly rearranged by substituting $z'=qp'$ where q is the fringe shift expressed in terms of fringe fraction; and $p'$, the pitch of the fringes, is given for small angles $\theta$ by $p/\theta$, where p is the pitch of the gratings. We obtain:

$$\beta = 9p/(2\Delta M) \quad (2)$$

Figure 5:
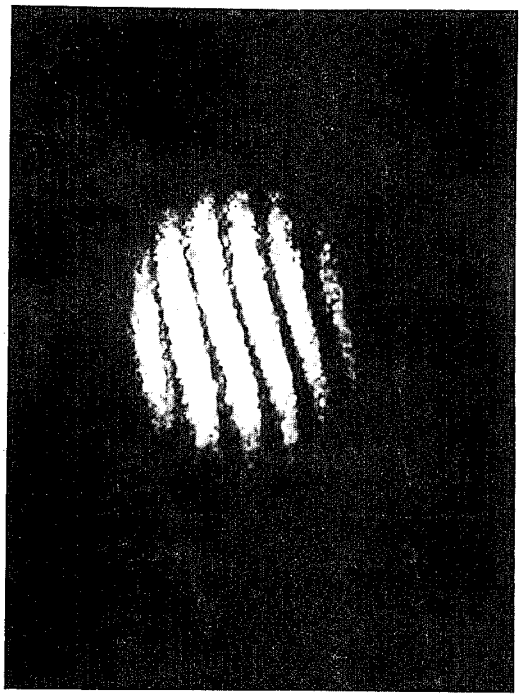
FIG. 5 illustrates a moire deflectrogram of a spherical mirror in accordance with the apparatus of FIG. 4.

FIG. 5 is a deflectogram of a spherical test mirror obtained with a setup similar to that of FIG. 4. The tested mirror diameter is 3″, and the f-number is 6. The focal length of the small objective lens is 6 cm. The gratings are Ronchi rulings with density of 40 lines/mm, and the distance between them is 20 mm. The gratings are mounted on a 1″-aperture commercial deflectometer produced by Rotlex Optics Ltd. In this arrangement, $M=7.5$; therefore, a unit fringe shift corresponds to a deviation of $8.0 \times 10^{-5}$ rad from a perfect spherical surface. The visual detection limit is about one tenth of a fringe; therefore the sensitivity is around $8.0 \times 10^{-6}$ rad (with techniques like heterodyne or phase shift, an improvement of one order of magnitude can be obtained). In the deflectogram of FIG. 5, distortions of up to 0.2 fringes can be observed, which means that the slope is aspheric by $1.6 \times 10^{-5}$ rad. Since the slope function is anti-symmetric, this means that a symmetric asphericity is located at the center of the lens.

In the new setup, the additional optical components (the flat mirror and the small objective lens) may introduce aberrations, and should therefore be of high optical quality. However, this setup is far more practical than those presented earlier due to the easy switching between the different modes of operation. The main advantage of the new setup, nevertheless, is the capability of high sensitivity measurement of large spherical mirrors, with a small aperture (1″-diameter) low cost optical system.

While the invention has been described with respect to two preferred embodiments, it will be appreciated that many other variations, modifications and applications of the invention may be made.

What is claimed is:

1. A method of optically examining an object, comprising the steps:
   providing a point source of light producing a diverging beam of direct light;
   directing the diverging beam of direct light to a first optical system including the object to be examined, which system retraces the light in the form of a converging beam of reflected light from the examined object back towards the point source of light;
   intercepting the converging beam of reflected light before reaching said point source of light;
   passing said intercepted converging beam of reflecting light through a second optical system which collimates the beam of reflected light;
   and examining said collimated beam of reflected light.

2. The method according to claim 1, wherein said object to be examined is a specular object having a curved specular surface; said retracing step being effected by reflecting the diverging beam from said curved specular surface of the examined object.

3. The method according to claim 1, wherein said step of intercepting the converging beam of reflected light is effected by a beam splitter through which passes the diverging beam from said point source of light.

4. The method according to claim 1, wherein the focal length of said first optical system is larger than that of the second optical system to reduce the image directed through said first and second gratings.

5. The method according to claim 1, wherein said point source of light is a laser producing a collimated beam of light.

6. The method according to claim 1, wherein said collimated beam of reflected light is examined by directing the collimated beam through first and second gratings at a preselected angular orientation and distance with respect to each other to produce moire fringe patterns providing an indication of the properties of the examined object.

7. The method according to claim 1, wherein said object to be examined included in said optical system is a phase object; said retracing of the light in the form of a converging beam being effected by collimating the diverging light beam from the point source before passing through the phase object, reflecting the collimated light beam back through the phase object, and converging the collimated light beam after passing back through the phase object.

8. The method according to claim 7, wherein the diverging light beam is passed in one direction through an objective lens to collimate it before passing through the phase object, and the collimated light beam is passed in the opposite direction through said objective lens to converge it after passing through the phase object.

9. The method according to claim 7, including the further step of maintaining paraxial approximation condition by moving said objective lens towards or away from said point source.

10. Optical examination apparatus for determining properties of an object comprising:
a point source of light producing a diverging beam of direct light;
a first optical system located such that, when it includes the object to be examined and receives the beam of direct light, it retraces the light in the form of a converging beam of reflected light from the examined object back towards the point source of light;
means for intercepting the converging beam of reflected light before reaching said point source of light;
a viewing device;
and a second optical system located to receive said intercepted beam of reflected light, to collimate it, and to direct the collimated beam to said viewing device.

11. The apparatus according to claim 10, wherein said objective lens is mounted for translation towards and away from the point source in order to fulfill paraxial approximation condition.

12. The apparatus according to claim 10, wherein the focal length of said first optical system is larger than that of the second optical system to reduce the image directed through said first and second gratings.

13. The apparatus according to claim 10, wherein said point source of light is a laser producing a collimated beam of light.

14. The apparatus according to claim 10, further including first and second gratings at a preselected angular orientation and separation with respect to each other located between said viewing device and said second optical system, such that the second optical system directs the collimated beam of reflected light through said first and second gratings to produce moire ray patterns providing an indication of the properties of the examined object.

15. The apparatus according to claim 10, wherein said intercepting means comprises a beam splitter.

16. The apparatus according to claim 10, wherein said first optical system includes a reflecting surface and an objective lens for collimating the diverging light beam from the point source before passing through the examined object, reflecting the collimated light beam from said reflecting surface, and converging the collimated light beam towards said point source of light.

17. The apparatus according to claim 15, wherein said second optical system comprises an objective lens which collimates the beam received from the beam splitter before directing said beam through said first and second gratings.

18. The apparatus according to claim 16, including means for supporting the examined object, being a phase object, between the objective lens and said reflecting surface, said light beam thereby being passed twice through the examined object.

19. The apparatus according to claim 16, wherein said reflecting surface is the examined object.

* * * * *